United States Patent [19]

Zipperer et al.

[11] Patent Number: 5,266,579
[45] Date of Patent: * Nov. 30, 1993

[54] CERTAIN PYRIDINE DERIVATIVES AND THE USE THEREOF AS FUNGICIDES

[75] Inventors: Bernhard Zipperer, Dirmstein; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[*] Notice: The portion of the term of this patent subsequent to May 12, 2009 has been disclaimed.

[21] Appl. No.: 831,440

[22] Filed: Feb. 5, 1992

Related U.S. Application Data

[63] Continuation of Ser. No. 502,401, Mar. 30, 1990, Pat. No. 5,112,828.

[30] Foreign Application Priority Data

May 5, 1989 [DE] Fed. Rep. of Germany ....... 3914820

[51] Int. Cl.$^5$ .................. A01N 43/40; C07D 405/06; C07D 409/06; C07D 213/55
[52] U.S. Cl. ..................... 514/336; 514/277; 546/268; 546/283; 546/284; 546/335; 546/342; 546/344
[58] Field of Search ............... 546/268, 283, 284, 335, 546/342, 344; 514/277, 336

[56] References Cited

U.S. PATENT DOCUMENTS 4,999,357  3/1991  Gadras et al. ................. 514/277
5,112,828  5/1992  Zipperer et al. ............... 514/277

Primary Examiner—Alan L. Rotman
Attorney, Agent, or Firm—Oblon, Spivak, McClelland, Maier & Neustadt

[57] ABSTRACT

Pyridines of the formula

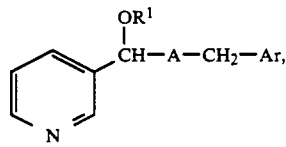

where $R^1$ is hydrogen, $C_1$-$C_6$-alkyl, $C_3$-$C_6$-alkenyl, $C_3$-$C_6$-alkynyl or an acyl radical $COR^2$; $R^2$ is $C_1$-$C_6$-alkyl, $C_3$-$C_6$-alkenyl, $C_3$-$C_6$-alkynyl, $C_1$-$C_6$-haloalkyl or substituted or unsubstituted aryl; A is one of the groups

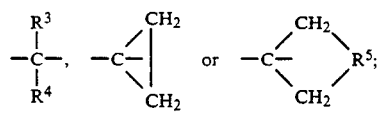

where $R^3$ and $R^4$ are identical or differ and each is $C_1$-$C_6$-alkyl, with the proviso that $R^3$ and $R^4$ are not simultaneously methyl; $R^5$ is one of the groups $(CH_2)_n$, $CH_2OCH_2$, $CH_2S(O)_mCH_2$, $CH_2CH_2O$ or $CH_2CH_2S(O)_m$, n denoting 1, 2, 3, 4 or 5, and m being 0, 1 or 2; Ar is aryl which is unsubstituted or bears from one to five substituents selected from the group consisting of $C_1$-$C_6$-alkyl, phenyl, halogen, $C_1$-$C_6$-haloalkyl, $C_1$-$C_6$-alkoxy, $C_1$-$C_6$-haloalkoxy, $C_1$-$C_6$-alkoxyiminocarbyl, phenoxy, halophenoxy and benzyloxy, and the N-oxides and plant-tolerated acid addition salts thereof, and fungicides containing these compounds.

3 Claims, No Drawings

CERTAIN PYRIDINE DERIVATIVES AND THE USE THEREOF AS FUNGICIDES

This is a continuation of application Ser. No. 07/502,401, filed on Mar. 30, 1990, now U.S. Pat. No. 5,112,828.

The present invention relates to novel pyridine derivatives, the N-oxides and salts thereof, to a process for the preparation thereof and the use thereof for controlling fungi.

The novel pyridine derivatives have the formula

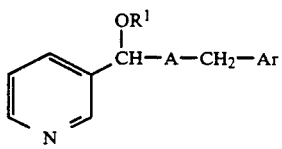

where
R$^1$ is hydrogen, C$_1$–C$_6$-alkyl, C$_3$–C$_6$-alkenyl, C$_3$–C$_6$-alkynyl or COR$^2$;
R$^1$ is C$_1$–C$_6$-alkyl, C$_3$–C$_6$-alkenyl, C$_3$–C$_6$-alkynyl, C$_1$–C$_6$-haloalkyl or substituted or unsubstituted aryl;
A is

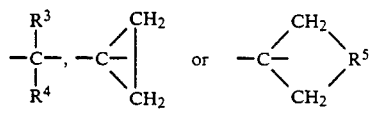

R$^3$ and R$^4$ are, independently of one another, C$_1$–C$_6$-alkyl with the proviso that R$^3$ and R$^4$ are not both methyl;
R$^5$ is (CH$_2$)$_n$, CH$_2$OCH$_2$, CH$_2$S(O)$_m$CH$_2$, CH$_2$CH$_2$O, CH$_2$CH$_2$S(O)$_m$ where
n is an integer from 1 to 5 and
m is an integer from 0 to 2;
Ar is aryl which carries 0–5 substituents from the group comprising C$_1$–C$_6$-alkyl, phenyl, halogen, C$_1$–C$_6$-haloalkyl, C$_1$–C$_6$-alkoxy, C$_1$–C$_6$-haloalkoxy, C$_1$–C$_6$-alkoxyiminomethyl, phenoxy, halophenoxy and benzyloxy, and the N-oxides and the acid addition salts which are tolerated by plants of the pyridine compounds.

Examples of R$^1$ are hydrogen, methyl, ethyl, n-propyl, isopropyl, n-butyl, isobutyl, tert-butyl, n-pentyl, iso-pentyl, n-hexyl; allyl, 2-methylallyl, 3-methylallyl, 3,3-dimethylallyl; propargyl.

Examples of R$^2$ are methyl, ethyl, n-propyl, isopropyl, n-butyl, isobutyl, tert-butyl, n-pentyl, isopentenyl, neo-pentyl, n-hexyl; trifluoromethyl, chloromethyl, dichloromethyl, trichloromethyl, bromomethyl, 2-bromoethyl, 2-chloroethyl, 3-bromopropyl, 4-bromobutyl; aryl which carries zero to three substituents selected from the group comprising C$_1$–C$_4$-alkyl, C$_1$–C$_4$-alkoxy, C$_1$–C$_4$-haloalkyl, halogen, cyano and nitro, such as naphthyl, phenyl, mono-, di- or trimethylphenyl, 4-tert-butylphenyl, mono-, di- or trimethoxyphenyl, trifluoromethylphenyl, fluorophenyl, mono-, di- or trichlorophenyl, mono- or dinitrophenyl and cyanophenyl.

Examples of R$^3$ and R$^4$ are, independently of one another, methyl, ethyl, n-propyl, isopropyl, n-butyl, isobutyl, tert-butyl, n-pentyl, isopentyl and n-hexyl.

Examples of R$^5$ are methylene, ethylene, 1,3-propylene, 1,4-butylene, 1,5-pentylene, oxydimethylene, ethyleneoxy, thiodimethylene, sulfinyldimethylene, sulfonyldimethylene, ethylenethio, ethylenesulfinyl and ethylenesulfonyl.

Examples of Ar are phenyl, naphthyl, indanyl, mono-, di-, tri- or tetramethylphenyl, ethylphenyl, propylphenyl, isopropylphenyl, butylphenyl, tert-butylphenyl, biphenyl, methylnaphthyl, mono- or difluorophenyl, methylfluorophenyl, tri-, tetra- or pentafluorophenyl, fluorochlorophenyl, methylchlorophenyl, mono-, di-, tri-, tetra- or pentachlorophenyl, bromophenyl, fluorobromophenyl, mono- or bis-trifluoromethylphenyl, mono-, di- or trimethoxyphenyl, ethoxyphenyl, trifluoromethoxyphenyl, tetrafluoroethoxyphenyl, methoxyiminomethylphenyl, ethoxyiminomethylphenyl, phenoxyphenyl, fluorophenoxyphenyl, chlorophenoxyphenyl, chlorophenoxychlorophenyl and benzyloxyphenyl.

Preferred compounds of the formula 1 are those in which
R$^1$ is hydrogen, methyl, ethyl, tert-butyl, allyl, propargyl or COR$^2$,
R$^2$ is C$_1$–C$_6$-alkyl, C$_1$–C$_6$-haloalkyl or substituted or unsubstituted phenyl,
A is

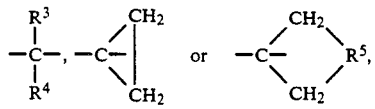

R$^3$ and R$^4$ are, independently of one another, methyl, ethyl, n-propyl, n-butyl, n-pentyl and n-hexyl,
R$^5$ is ethylene or 1,3-propylene, and Ar has the meanings specified in claim 1.

The present invention also relates to the N-oxides and the acid addition salts which are tolerated by plants of the novel pyridine derivatives. Examples of salts which are tolerated by plants of the pyridines are salts with mineral acids such as hydrochlorides, hydrobromides, sulfates, nitrates and phosphates; salts with alkanecarboxylic acids such as formates, acetates, propionates, 2-ethylhexanoates and oxalates; salts with arenesulfonic acids such as benzenesulfonates, toluenesulfonates and dodecylbenzenesulfonates.

The compounds of the formula 1 can contain two centers of asymmetry and thus exist in two diastereomeric forms which can be separated by conventional processes, for example by chromatography or crystallization. The present invention embraces both the individual diastereomers and the mixtures thereof and fungicides containing these compounds.

The compounds of the formula 1 have a good fungicidal action which is better than the action of conventional fungicides.

The use of pyridylcarbinols, e.g. 3-phenyl-2,2-dimethyl-1-(3-pyridyl)-1-propanol which is disclosed in EP 302 365, as fungicides has been disclosed. Their fungicidal action is, however, not always entirely satisfactory for certain indications, especially at low application rates.

The process for the preparation of the novel compounds of the formula 1 comprises an aldehyde of the formula 2

Ar—CH$_2$—A—CHO      2 in which Ar and A have the meanings specified in claim 1, being reacted with an organometallic compound of the formula 3

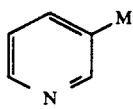

in which M is lithium or MgCl, MgBr or MgI, and the resulting pyridyl alcohol of the formula 1 in which A and Ar have the meanings specified in claim 1, and $R^1$ is hydrogen, being either alkylated with a compound of the formula 4 or acylated with a compound of the formula 5

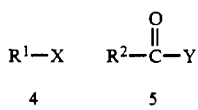

in which $R^1$ and $R^2$ have the meanings specified in claim 1 with the exception of hydrogen, and X and Y are nucleofugic groups.

Examples of X are chlorine, bromine, iodine, $OSO_2CH_3$, $OSO_2C_6H_5$ and $OSO_2$—$C_6H_4$—$CH_3$ (p).

Examples of Y are chlorine, bromine, iodine,

or 1-imidazolyl.

The procedure for this reaction is such that, for example, a mixture of pyridyl alcohol of the formula 1 in which $R^1$ is hydrogen is introduced into at least the equimolar amount of an auxiliary base, with or without an inert organic solvent such as diethyl ether, tetrahydrofuran, dioxane, dimethylformamide, dimethyl sulfoxide, acetonitrile, toluene or xylene, and then the alkylating or acylating agent is metered in.

The reaction is carried out at from 0° to 120° C., preferably 20° to 80° C., for example.

Auxiliary bases which can be used are inorganic and organic acid-binding agents.

Examples of inorganic bases are sodium hydride, sodamide, sodium hydroxide, sodium carbonate, potassium carbonate, potassium hydroxide etc.

Examples of organic bases are amines, especially tertiary amines such as triethylamine, ethyldiisopropylamine and pyridine, and alcoholates such as sodium methylate, sodium ethylate and potassium tert-butylate.

An occasionally advantageous variant of this process entails reacting the pyridyl alcohols of the formula 1 with alkylating agents of the formula 4 in a two-phase system composed of aqueous sodium hydroxide solution and an organic solvent, preferably toluene or dichloromethane, with the addition of a phase-transfer catalyst, e.g. tetra-n-butylammonium chloride, benzyltriethylammonium chloride or methyltrioctylammonium chloride.

The novel pyridyl alcohols of the formula 1 in which $R^1$ is hydrogen can be prepared, for example, by reacting a metalated pyridine of the formula 3 in which M is lithium or MgCl, MgBr or MgI with an aldehyde of the formula 2 in which Ar and A have the meanings specified in claim 1, e.g. in the presence of a suitable solvent.

This advantageously entails the organometallic compound of the formula 3 being introduced into an inert solvent, preferably an ether such as diethyl ether or tetrahydrofuran, at from −100° to +20° C., preferably from −70° to 0° C., and adding the aldehyde of the formula 2, which may be dissolved in a diluent, dropwise.

The metalated pyridines of the formula 3 are known and can be prepared from the corresponding 3-halopyridines (cf. e.g. N. Furukawa et al., Tetrahedron Letters 1987, 5845 for M=MgBr; A. Fischer and M. W. Morgan, J. Organomet. Chem. 136 (1977) 323 for M=Li).

Some of the aldehydes of the formula 2 are known, and they can be prepared by known processes by alkylating aldehydes of the formula 6 in which A has the meanings specified in claim 1 with a benzyl halide of the formula 7:

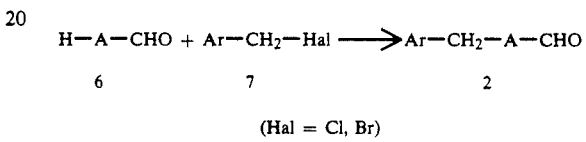

(Hal = Cl, Br)

It is known that direct α-alkylation of aldehydes usually takes place with only poor yields; the same applies to the enamines derived from the aldehydes (cf. e.g. G. Opitz et al., Liebigs Ann. Chem. 649 (1961) 36). Better results are obtained when the aldehydes of the formula 6 are first converted into N-metalated imines which are then alkylated with benzyl halides (cf. H. Normant et al., Bull. Soc. Chim. Fr. 1970, 3976). A more straightforward method is phase-transfer catalyzed α-alkylation of aldehydes. This process can be carried out as the solid/liquid variant in a two-phase system composed of solid sodium hydroxide and a lipophilic organic solvent (cf. V. G. Poruhit and R. Subramanian, Chem. Ind. (London) 1978, 731) or as the liquid/liquid variant in a two-phase system composed of concentrated sodium hydroxide solution and a lipophilic organic solvent (cf. H. K. Dietl and K. C. Brannock, Tetrahedron Lett. 1973, 1273; E. Buschmann and B. Zeeh, Liebigs Ann. Chem. 1979, 1585).

Another process for the preparation of aldehydes of the formula 2 comprises alkylating nitriles of the formula 8 with benzyl halides of the formula 7, and converting the reaction products of the formula 9 with a suitable reducing agent into the aldehydes 2:

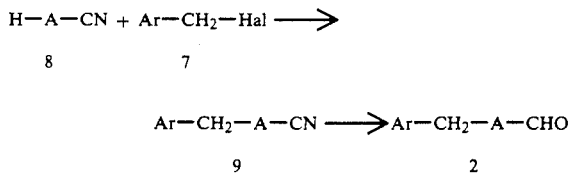

The α-alkylation of nitriles and the reduction of nitriles to aldehydes are known reactions (cf. e.g. D. S. Watt et al., Org. React. 31 (1984) 1 et seq.; M. Rabinovitz in Z. Rappoport (Ed.) "The Chemistry of the Cyano Group", pp. 307 et seq., Interscience, New York 1970; J. Malek and M. Cerny, Synthesis 1972, 217; N. M. Yoon and Y. S. Gyoung, J. Org. Chem. 50 (1985) 2443).

The aldehydes 6, nitriles 8 and benzyl halides 7 used as starting materials are known, and most of them are commercially available.

The examples which follow illustrate the preparation of the novel pyridine derivatives.

EXAMPLE 1

2-(4-Chlorobenzyl)-2-ethyl-1-(3-pyridyl)butyl acetate (compound no. 611)

10.2 g (0.10 mol) of acetic anhydride are added dropwise to a solution of 12.1 g (0.04 mol) of 2-(4-chlorobenzyl)-2-ethyl-1-(3-pyridyl)-1-butanol in 50 ml of pyridine at room temperature, and the mixture is then heated at 80° C. for 8 h. The reaction mixture is concentrated, the residue is taken up in 200 ml of dichloromethane, and the solution is washed with saturated NaHCO$_3$ solution and then with water. The organic phase is dried and concentrated, and the remaining black oil is purified on silica gel (mobile phase: 5:1 cyclohexane/ethyl acetate). 11.2 g (81% of theory) of the title compound are obtained as a viscous yellow oil. $^1$H-NMR (CDCl$_3$): δ=8.60(2-Hpy), 8.52(6-Hpy), 7.65(4-Hpy), 7.30(5-Hpy), 7.25(2Hm), 7.05(2Ho), 5.62(CHOAc), 2.68(CH$_2$Ar), 2.08(COCH$_3$), 1.45(CH$_2$), 1.30(CH$_2$), 0.95(CH$_3$), 0.83(CH$_3$).

EXAMPLE 2

2-(4-Chlorobenzyl)-2-ethyl-1-(3-pyridyl)-1-butanol (compound no. 113)

A solution of 15.8 g of 3-bromopyridine (0.10 mol) in 50 ml of diethyl ether is added dropwise to a mixture of 82 ml of a 1.6M n-butyllithium solution in n-hexane (0.13 mol) under a nitrogen atmosphere at −70° C. The mixture is stirred at −70° C. for 10 minutes and then a solution of 24.7 g of 2-(4-chlorobenzyl)-2-ethylbutanal (0.11 mol) in 50 ml of diethyl ether is added dropwise. After 1 h at −70° C., the mixture is allowed to warm slowly to room temperature and is hydrolyzed with saturated aqueous ammonium chloride solution. The mixture is acidified with dilute hydrochloric acid, and the aqueous phase is separated off and washed with ether and then adjusted to pH 10 to 11 with concentrated ammonia solution while cooling. It is extracted three times with dichloromethane, and the organic phase is dried over Na$_2$SO$_4$ and concentrated. The solid crude product is recrystallized from ethyl acetate/hexane (1:1). 19.2 g (63% of theory) of colorless crystals of melting point 128°-129° C.

Preparation of the starting compound 2-(4-Chlorobenzyl)-2-ethylbutanal 300 ml of toluene, 400 ml of 30 percent (by weight) sodium hydroxide solution and 5.0 g of tetra-n-butylammonium iodide are heated at 80° C. while stirring. To this is slowly added dropwise a mixture of 110 g (1.10 mol) of 2-ethylbutanal and 161 g (1.00 mol) of 4-chlorobenzyl chloride. The mixture is then stirred at 80° C. for 4 h and at room temperature for 14 h, 1,000 ml of toluene are added, and the phases are separated. The organic phase is washed with water, dried over Na$_2$SO$_4$ and concentrated. Fractional distillation results in 123 g (54% of theory) of 2-(4-chlorobenzyl)-2-ethylbutanal as a colorless liquid of boiling point 146°-148° C. at 1 mbar.

The following compounds can also be prepared in a manner corresponding to that in Examples 1 and 2:

TABLE 1

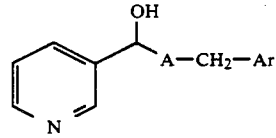

| Ex. no. | A | Ar | Physical data |
|---|---|---|---|
| 1 | C(CH$_3$)C$_2$H$_5$ | phenyl | |
| 2 | C(CH$_3$)C$_2$H$_5$ | 2-methylphenyl | |
| 3 | C(CH$_3$)C$_2$H$_5$ | 3-methylphenyl | |
| 4 | C(CH$_3$)C$_2$H$_5$ | 4-methylphenyl | |
| 5 | C(CH$_3$)C$_2$H$_5$ | 2,3-dimethylphenyl | |
| 6 | C(CH$_3$)C$_2$H$_5$ | 2,4-dimethylphenyl | |
| 7 | C(CH$_3$)C$_2$H$_5$ | 2,5-dimethylphenyl | |
| 8 | C(CH$_3$)C$_2$H$_5$ | 2,6-dimethylphenyl | |
| 9 | C(CH$_3$)C$_2$H$_5$ | 3,4-dimethylphenyl | |
| 10 | C(CH$_3$)C$_2$H$_5$ | 3,5-dimethylphenyl | |
| 11 | C(CH$_3$)C$_2$H$_5$ | 2,4,5-trimethylphenyl | |
| 12 | C(CH$_3$)C$_2$H$_5$ | 2,4,6-trimethylphenyl | |
| 13 | C(CH$_3$)C$_2$H$_5$ | 2,3,5,6-tetramethylphenyl | |
| 14 | C(CH$_3$)C$_2$H$_5$ | 4-ethylphenyl | |
| 15 | C(CH$_3$)C$_2$H$_5$ | 4-isopropylphenyl | |
| 16 | C(CH$_3$)C$_2$H$_5$ | 4-tert.butylphenyl | |
| 17 | C(CH$_3$)C$_2$H$_5$ | 5-indanyl | |
| 18 | C(CH$_3$)C$_2$H$_5$ | 1-naphthyl | |
| 19 | C(CH$_3$)C$_2$H$_5$ | 2-naphthyl | |
| 20 | C(CH$_3$)C$_2$H$_5$ | 2-methyl-1-naphthyl | |
| 21 | C(CH$_3$)C$_2$H$_5$ | 4-biphenyl | |
| 22 | C(CH$_3$)C$_2$H$_5$ | 2-fluorophenyl | |
| 23 | C(CH$_3$)C$_2$H$_5$ | 3-fluorophenyl | |
| 24 | C(CH$_3$)C$_2$H$_5$ | 4-fluorophenyl | |
| 25 | C(CH$_3$)C$_2$H$_5$ | 2,3-difluorophenyl | |
| 26 | C(CH$_3$)C$_2$H$_5$ | 2,4-difluorophenyl | |
| 27 | C(CH$_3$)C$_2$H$_5$ | 2,5-difluorophenyl | |
| 28 | C(CH$_3$)C$_2$H$_5$ | 2,6-difluorophenyl | |
| 29 | C(CH$_3$)C$_2$H$_5$ | 3,4-difluorophenyl | |
| 30 | C(CH$_3$)C$_2$H$_5$ | 3,5-difluorophenyl | |
| 31 | C(CH$_3$)C$_2$H$_5$ | 2-fluoro-3-methylphenyl | |
| 32 | C(CH$_3$)C$_2$H$_5$ | 2,3,5,6-tetrafluorophenyl | |
| 33 | C(CH$_3$)C$_2$H$_5$ | pentafluorophenyl | |
| 34 | C(CH$_3$)C$_2$H$_5$ | 2-chlorophenyl | |
| 35 | C(CH$_3$)C$_2$H$_5$ | 3-chlorophenyl | |
| 36 | C(CH$_3$)C$_2$H$_5$ | 4-chlorophenyl | |
| 37 | C(CH$_3$)C$_2$H$_5$ | 2,3-dichlorophenyl | |
| 38 | C(CH$_3$)C$_2$H$_5$ | 2,4-dichlorophenyl | |
| 39 | C(CH$_3$)C$_2$H$_5$ | 2,5-dichlorophenyl | |
| 40 | C(CH$_3$)C$_2$H$_5$ | 2,6-dichlorophenyl | |
| 41 | C(CH$_3$)C$_2$H$_5$ | 3,4-dichlorophenyl | |
| 42 | C(CH$_3$)C$_2$H$_5$ | 3,5-dichlorophenyl | |
| 43 | C(CH$_3$)C$_2$H$_5$ | 2,4,5-trichlorophenyl | |
| 44 | C(CH$_3$)C$_2$H$_5$ | 2,4,6-trichlorophenyl | |
| 45 | C(CH$_3$)C$_2$H$_5$ | 2,3,6-trichlorophenyl | |
| 46 | C(CH$_3$)C$_2$H$_5$ | 2-chloro-5-methylphenyl | |
| 47 | C(CH$_3$)C$_2$H$_5$ | 3-chloro-4-methylphenyl | |
| 48 | C(CH$_3$)C$_2$H$_5$ | 2-chloro-4-fluorophenyl | |
| 49 | C(CH$_3$)C$_2$H$_5$ | 2-chloro-6-fluorophenyl | |
| 50 | C(CH$_3$)C$_2$H$_5$ | 3-chloro-2-fluorophenyl | |
| 51 | C(CH$_3$)C$_2$H$_5$ | pentachlorophenyl | |
| 52 | C(CH$_3$)C$_2$H$_5$ | 2-bromophenyl | |
| 53 | C(CH$_3$)C$_2$H$_5$ | 3-bromophenyl | |
| 54 | C(CH$_3$)C$_2$H$_5$ | 4-bromophenyl | |
| 55 | C(CH$_3$)C$_2$H$_5$ | 2-fluoro-4-bromophenyl | |
| 56 | C(CH$_3$)C$_2$H$_5$ | 2-trifluoromethylphenyl | |
| 57 | C(CH$_3$)C$_2$H$_5$ | 3-trifluoromethylphenyl | |
| 58 | C(CH$_3$)C$_2$H$_5$ | 4-trifluoromethylphenyl | |
| 59 | C(CH$_3$)C$_2$H$_5$ | 2,4-bis(trifluoromethyl)phenyl | |
| 60 | C(CH$_3$)C$_2$H$_5$ | 3,5-bis(trifluoromethyl)phenyl | |
| 61 | C(CH$_3$)C$_2$H$_5$ | 2-methoxyphenyl | |
| 62 | C(CH$_3$)C$_2$H$_5$ | 3-methoxyphenyl | |
| 63 | C(CH$_3$)C$_2$H$_5$ | 4-methoxyphenyl | |
| 64 | C(CH$_3$)C$_2$H$_5$ | 3,4-dimethoxyphenyl | |
| 65 | C(CH$_3$)C$_2$H$_5$ | 3,4,5-trimethoxyphenyl | |
| 66 | C(CH$_3$)C$_2$H$_5$ | 4-ethoxyphenyl | |
| 67 | C(CH$_3$)C$_2$H$_5$ | 4-tetrafluoroethoxyphenyl | |
| 68 | C(CH$_3$)C$_2$H$_5$ | 4-trifluoromethoxyphenyl | |
| 69 | C(CH$_3$)C$_2$H$_5$ | 4-methoxyiminocarbyl-phenyl | |
| 70 | C(CH$_3$)C$_2$H$_5$ | 4-ethoxyiminocarbyl-phenyl | |
| 71 | C(CH$_3$)C$_2$H$_5$ | 4-methoxy-3-methylphenyl | |
| 72 | C(CH$_3$)C$_2$H$_5$ | 3-phenoxyphenyl | |

TABLE 1-continued

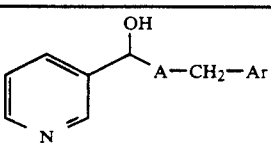

| Ex. no. | A | Ar | Physical data |
|---|---|---|---|
| 73 | C(CH₃)C₂H₅ | 4-phenoxyphenyl | |
| 74 | C(CH₃)C₂H₅ | 2-chloro-4-(4'-chloro-phenoxy)phenyl | |
| 75 | C(CH₃)C₂H₅ | 4-(4'-chlorophenoxy)-phenyl) | |
| 76 | C(CH₃)C₂H₅ | 3-(4'-fluorophenoxy)-phenyl | |
| 77 | C(CH₃)C₂H₅ | 4-benzyloxyphenyl | |
| 78 | C(C₂H₅)₂ | phenyl | mp. 130–132 |
| 79 | C(C₂H₅)₂ | 2-methylphenyl | mp. 92–94 |
| 80 | C(C₂H₅)₂ | 3-methylphenyl | |
| 81 | C(C₂H₅)₂ | 4-methylphenyl | mp. 87–88 |
| 82 | C(C₂H₅)₂ | 2,3-dimethylphenyl | |
| 83 | C(C₂H₅)₂ | 2,4-dimethylphenyl | |
| 84 | C(C₂H₅)₂ | 2,5-dimethylphenyl | |
| 85 | C(C₂H₅)₂ | 2,6-dimethylphenyl | |
| 86 | C(C₂H₅)₂ | 3,4-dimethylphenyl | |
| 87 | C(C₂H₅)₂ | 3,5-dimethylphenyl | |
| 88 | C(C₂H₅)₂ | 2,4,5-trimethylphenyl | |
| 89 | C(C₂H₅)₂ | 2,4,6-trimethylphenyl | |
| 90 | C(C₂H₅)₂ | 2,3,5,6-tetramethylphenyl | |
| 91 | C(C₂H₅)₂ | 4-ethylphenyl | |
| 92 | C(C₂H₅)₂ | 4-isopropylphenyl | |
| 93 | C(C₂H₅)₂ | 4-tert.butylphenyl | mp. 122–124 |
| 94 | C(C₂H₅)₂ | 5-indanyl | |
| 95 | C(C₂H₅)₂ | 1-naphthyl | mp. 112–113 |
| 96 | C(C₂H₅)₂ | 2-naphthyl | |
| 97 | C(C₂H₅)₂ | 2-methyl-1-naphthyl | |
| 98 | C(C₂H₅)₂ | 4-biphenyl | |
| 99 | C(C₂H₅)₂ | 2-fluorophenyl | |
| 100 | C(C₂H₅)₂ | 3-fluorophenyl | mp. 120–122 |
| 101 | C(C₂H₅)₂ | 4-fluorophenyl | mp. 148–150 |
| 102 | C(C₂H₅)₂ | 2,3-difluorophenyl | |
| 103 | C(C₂H₅)₂ | 2,4-difluorophenyl | |
| 104 | C(C₂H₅)₂ | 2,5-difluorophenyl | |
| 105 | C(C₂H₅)₂ | 2,6-difluorophenyl | |
| 106 | C(C₂H₅)₂ | 3,4-difluorophenyl | |
| 107 | C(C₂H₅)₂ | 3,5-difluorophenyl | |
| 108 | C(C₂H₅)₂ | 2-fluoro-3-methylphenyl | |
| 109 | C(C₂H₅)₂ | 2,3,5,6-tetrafluorophenyl | |
| 110 | C(C₂H₅)₂ | pentafluorophenyl | |
| 111 | C(C₂H₅)₂ | 2-chlorophenyl | mp. 96–98 |
| 112 | C(C₂H₅)₂ | 3-chlorophenyl | |
| 113 | C(C₂H₅)₂ | 4-chlorophenyl | mp. 128–129 |
| 114 | C(C₂H₅)₂ | 2,3-dichlorophenyl | |
| 115 | C(C₂H₅)₂ | 2,4-dichlorophenyl | mp. 139–140 |
| 116 | C(C₂H₅)₂ | 2,5-dichlorophenyl | |
| 117 | C(C₂H₅)₂ | 2,6-dichlorophenyl | |
| 118 | C(C₂H₅)₂ | 3,4-dichlorophenyl | |
| 119 | C(C₂H₅)₂ | 3,5-dichlorophenyl | |
| 120 | C(C₂H₅)₂ | 2,4,5-trichlorophenyl | |
| 121 | C(C₂H₅)₂ | 2,4,6-trichlorophenyl | |
| 122 | C(C₂H₅)₂ | 2,3,6-trichlorophenyl | |
| 123 | C(C₂H₅)₂ | 2-chloro-5-methylphenyl | |
| 124 | C(C₂H₅)₂ | 3-chloro-4-methylphenyl | |
| 125 | C(C₂H₅)₂ | 2-chloro-4-fluorophenyl | |
| 126 | C(C₂H₅)₂ | 2-chloro-6-fluorophenyl | |
| 127 | C(C₂H₅)₂ | 3-chloro-2-fluorophenyl | |
| 128 | C(C₂H₅)₂ | pentachlorophenyl | |
| 129 | C(C₂H₅)₂ | 2-bromophenyl | |
| 130 | C(C₂H₅)₂ | 3-bromophenyl | |
| 131 | C(C₂H₅)₂ | 4-bromophenyl | |

TABLE 1-continued

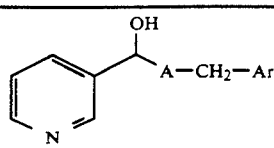

| Ex. no. | A | Ar | Physical data |
|---|---|---|---|
| 132 | C(C₂H₅)₂ | 2-fluoro-4-bromophenyl | |
| 133 | C(C₂H₅)₂ | 2-trifluoromethylphenyl | |
| 134 | C(C₂H₅)₂ | 3-trifluoromethylphenyl | |
| 135 | C(C₂H₅)₂ | 4-trifluoromethylphenyl | |
| 136 | C(C₂H₅)₂ | 2,4-bis(trifluoromethyl)phenyl | |
| 137 | C(C₂H₅)₂ | 3,5-bis(trifluoromethyl)phenyl | |
| 138 | C(C₂H₅)₂ | 2-methoxyphenyl | |
| 139 | C(C₂H₅)₂ | 3-methoxyphenyl | |
| 140 | C(C₂H₅)₂ | 4-methoxyphenyl | |
| 141 | C(C₂H₅)₂ | 3,4-dimethoxyphenyl | |
| 142 | C(C₂H₅)₂ | 3,4,5-trimethoxyphenyl | |
| 143 | C(C₂H₅)₂ | 4-ethoxyphenyl | |
| 144 | C(C₂H₅)₂ | 4-tetrafluoroethoxyphenyl | |
| 145 | C(C₂H₅)₂ | 4-trifluoromethoxyphenyl | |
| 146 | C(C₂H₅)₂ | 4-methoxyiminocarbyl-phenyl | |
| 147 | C(C₂H₅)₂ | 4-ethoxyiminocarbyl-phenyl | |
| 148 | C(C₂H₅)₂ | 4-methoxy-3-methylphenyl | |
| 149 | C(C₂H₅)₂ | 3-phenoxyphenyl | |
| 150 | C(C₂H₅)₂ | 4-phenoxyphenyl | |
| 151 | C(C₂H₅)₂ | 2-chloro-4-(4'-chloro-phenoxy)phenyl | |
| 152 | C(C₂H₅)₂ | 4-(4'-chlorophenoxy)-phenyl) | |
| 153 | C(C₂H₅)₂ | 4-benzyloxyphenyl | |
| 154 | C(CH₂)₄ | phenyl | |
| 155 | C(CH₂)₄ | 2-methylphenyl | |
| 156 | C(CH₂)₄ | 3-methylphenyl | |
| 157 | C(CH₂)₄ | 4-methylphenyl | |
| 158 | C(CH₂)₄ | 2,3-dimethylphenyl | |
| 159 | C(CH₂)₄ | 2,4-dimethylphenyl | |
| 160 | C(CH₂)₄ | 2,5-dimethylphenyl | |
| 161 | C(CH₂)₄ | 2,6-dimethylphenyl | |
| 162 | C(CH₂)₄ | 3,4-dimethylphenyl | |
| 163 | C(CH₂)₄ | 3,5-dimethylphenyl | |
| 164 | C(CH₂)₄ | 2,4,5-trimethylphenyl | |
| 165 | C(CH₂)₄ | 2,4,6-trimethylphenyl | |
| 166 | C(CH₂)₄ | 2,3,5,6-tetramethylphenyl | |
| 167 | C(CH₂)₄ | 4-ethylphenyl | |
| 168 | C(CH₂)₄ | 4-isopropylphenyl | |
| 169 | C(CH₂)₄ | 4-tert.butylphenyl | |
| 170 | C(CH₂)₄ | 5-indanyl | |
| 171 | C(CH₂)₄ | 1-naphthyl | |
| 172 | C(CH₂)₄ | 2-naphthyl | |
| 173 | C(CH₂)₄ | 2-methyl-1-napthyl | |
| 174 | C(CH₂)₄ | 4-biphenyl | |
| 175 | C(CH₂)₄ | 2-fluorophenyl | mp. 75–76 |
| 176 | C(CH₂)₄ | 3-fluorophenyl | |
| 177 | C(CH₂)₄ | 4-fluorophenyl | mp. 166–168 |
| 178 | C(CH₂)₄ | 2,3-difluorophenyl | |
| 179 | C(CH₂)₄ | 2,4-difluorophenyl | |
| 180 | C(CH₂)₄ | 2,5-difluorophenyl | |
| 181 | C(CH₂)₄ | 2,6-difluorophenyl | |
| 182 | C(CH₂)₄ | 3,4-difluorophenyl | |
| 183 | C(CH₂)₄ | 3,5-difluorophenyl | |
| 184 | C(CH₂)₄ | 2-fluoro-3-methylphenyl | |
| 185 | C(CH₂)₄ | 2,3,5,6-tetrafluorophenyl | |
| 186 | C(CH₂)₄ | pentafluorophenyl | |
| 187 | C(CH₂)₄ | 2-chlorophenyl | mp. 114–116 |
| 188 | C(CH₂)₄ | 3-chlorophenyl | |
| 189 | C(CH₂)₄ | 4-chlorophenyl | mp. 162–164 |
| 190 | C(CH₂)₄ | 2,3-dichlorophenyl | |
| 191 | C(CH₂)₄ | 2,4-dichlorophenyl | mp. 110–112 |
| 192 | C(CH₂)₄ | 2,5-dichlorophenyl | |
| 193 | C(CH₂)₄ | 2,6-dichlorophenyl | |
| 194 | C(CH₂)₄ | 3,4-dichlorophenyl | |
| 195 | C(CH₂)₄ | 3,5-dichlorophenyl | |
| 196 | C(CH₂)₄ | 2,4,5-trichlorophenyl | |

TABLE 1-continued

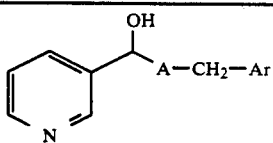

| Ex. no. | A | Ar | Physical data |
|---|---|---|---|
| 197 | $C(CH_2)_4$ | 2,4,6-trichlorophenyl | |
| 198 | $C(CH_2)_4$ | 2,3,6-trichlorophenyl | |
| 199 | $C(CH_2)_4$ | 2-chloro-5-methylphenyl | |
| 200 | $C(CH_2)_4$ | 3-chloro-4-methylphenyl | |
| 201 | $C(CH_2)_4$ | 2-chloro-4-fluorophenyl | |
| 202 | $C(CH_2)_4$ | 2-chloro-6-fluorophenyl | |
| 203 | $C(CH_2)_4$ | 3-chloro-2-fluorophenyl | |
| 204 | $C(CH_2)_4$ | pentachlorophenyl | |
| 205 | $C(CH_2)_4$ | 2-bromophenyl | |
| 206 | $C(CH_2)_4$ | 3-bromophenyl | |
| 207 | $C(CH_2)_4$ | 4-bromophenyl | |
| 208 | $C(CH_2)_4$ | 2-fluoro-4-bromophenyl | |
| 209 | $C(CH_2)_4$ | 2-trifluoromethylphenyl | |
| 210 | $C(CH_2)_4$ | 3-trifluoromethylphenyl | |
| 211 | $C(CH_2)_4$ | 4-trifluoromethylphenyl | |
| 212 | $C(CH_2)_4$ | 2,4-bis(trifluoromethyl)phenyl | |
| 213 | $C(CH_2)_4$ | 3,5-bis(trifluoromethyl)phenyl | |
| 214 | $C(CH_2)_4$ | 2-methoxyphenyl | |
| 215 | $C(CH_2)_4$ | 3-methoxyphenyl | |
| 216 | $C(CH_2)_4$ | 4-methoxyphenyl | |
| 217 | $C(CH_2)_4$ | 3,4-dimethoxyphenyl | |
| 218 | $C(CH_2)_4$ | 3,4,5-trimethoxyphenyl | |
| 219 | $C(CH_2)_4$ | 4-ethoxyphenyl | |
| 220 | $C(CH_2)_4$ | 4-tetrafluoroethoxyphenyl | |
| 221 | $C(CH_2)_4$ | 4-trifluoromethoxyphenyl | |
| 222 | $C(CH_2)_4$ | 4-methoxyiminocarbyl-phenyl | |
| 223 | $C(CH_2)_4$ | 4-ethoxyiminocarbyl-phenyl | |
| 224 | $C(CH_2)_4$ | 4-methoxy-3-methylphenyl | |
| 225 | $C(CH_2)_4$ | 3-phenoxyphenyl | |
| 226 | $C(CH_2)_4$ | 4-phenoxyphenyl | |
| 227 | $C(CH_2)_4$ | 2-chloro-4-(4'-chlorophenoxy)phenyl | |
| 228 | $C(CH_2)_4$ | 3-(4'-fluorophenoxy)-phenyl | |
| 229 | $C(CH_2)_4$ | 4-benzyloxyphenyl | |
| 230 | $C(CH_2)_5$ | phenyl | mp. 117-119 |
| 231 | $C(CH_2)_5$ | 2-methylphenyl | |
| 232 | $C(CH_2)_5$ | 3-methylphenyl | |
| 233 | $C(CH_2)_5$ | 4-methylphenyl | |
| 234 | $C(CH_2)_5$ | 2,3-dimethylphenyl | |
| 235 | $C(CH_2)_5$ | 2,4-dimethylphenyl | |
| 236 | $C(CH_2)_5$ | 2,5-dimethylphenyl | |
| 237 | $C(CH_2)_5$ | 2,6-dimethylphenyl | |
| 238 | $C(CH_2)_5$ | 3,4-dimethylphenyl | |
| 239 | $C(CH_2)_5$ | 3,5-dimethylphenyl | |
| 240 | $C(CH_2)_5$ | 2,4,5-trimethylphenyl | |
| 241 | $C(CH_2)_5$ | 2,4,6-trimethylphenyl | |
| 242 | $C(CH_2)_5$ | 2,3,5,6-tetramethylphenyl | |
| 243 | $C(CH_2)_5$ | 4-ethylphenyl | |
| 244 | $C(CH_2)_5$ | 4-isopropylphenyl | |
| 245 | $C(CH_2)_5$ | 4-tert.butylphenyl | |
| 246 | $C(CH_2)_5$ | 5-indanyl | |
| 247 | $C(CH_2)_5$ | 1-naphthyl | |
| 248 | $C(CH_2)_5$ | 2-naphthyl | |
| 249 | $C(CH_2)_5$ | 2-methyl-1-napthyl | |
| 250 | $C(CH_2)_5$ | 4-biphenyl | |
| 251 | $C(CH_2)_5$ | 2-fluorophenyl | mp. 146-148 |
| 252 | $C(CH_2)_5$ | 3-fluorophenyl | mp. 132-134 |
| 253 | $C(CH_2)_5$ | 4-fluorophenyl | mp. 126-127 |
| 254 | $C(CH_2)_5$ | 2,3-difluorophenyl | |
| 255 | $C(CH_2)_5$ | 2,4-difluorophenyl | |
| 256 | $C(CH_2)_5$ | 2,5-difluorophenyl | |
| 257 | $C(CH_2)_5$ | 2,6-difluorophenyl | |
| 258 | $C(CH_2)_5$ | 3,4-difluorophenyl | |
| 259 | $C(CH_2)_5$ | 3,5-difluorophenyl | |
| 260 | $C(CH_2)_5$ | 2-fluoro-3-methylphenyl | |
| 261 | $C(CH_2)_5$ | 2,3,5,6-tetrafluorophenyl | |
| 262 | $C(CH_2)_5$ | pentafluorophenyl | |

TABLE 1-continued

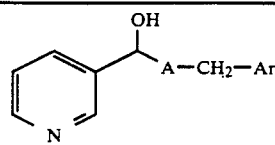

| Ex. no. | A | Ar | Physical data |
|---|---|---|---|
| 263 | $C(CH_2)_5$ | 2-chlorophenyl | mp. 162-164 |
| 264 | $C(CH_2)_5$ | 3-chlorophenyl | |
| 265 | $C(CH_2)_5$ | 4-chlorophenyl | mp. 155-156 |
| 266 | $C(CH_2)_5$ | 2,3-dichlorophenyl | |
| 267 | $C(CH_2)_5$ | 2,4-dichlorophenyl | oil; N-oxide mp. 205-207 |
| 268 | $C(CH_2)_5$ | 2,5-dichlorophenyl | |
| 269 | $C(CH_2)_5$ | 2,6-dichlorophenyl | |
| 270 | $C(CH_2)_5$ | 3,4-dichlorophenyl | mp. 181-183 |
| 271 | $C(CH_2)_5$ | 3,5-dichlorophenyl | |
| 272 | $C(CH_2)_5$ | 2,4,5-trichlorophenyl | |
| 273 | $C(CH_2)_5$ | 2,4,6-trichlorophenyl | |
| 274 | $C(CH_2)_5$ | 2,3,6-trichlorophenyl | |
| 275 | $C(CH_2)_5$ | 2-chloro-5-methylphenyl | |
| 276 | $C(CH_2)_5$ | 3-chloro-4-methylphenyl | |
| 277 | $C(CH_2)_5$ | 2-chloro-4-fluorophenyl | |
| 278 | $C(CH_2)_5$ | 2-chloro-6-fluorophenyl | |
| 279 | $C(CH_2)_5$ | 3-chloro-2-fluorophenyl | |
| 280 | $C(CH_2)_5$ | pentachlorophenyl | |
| 281 | $C(CH_2)_5$ | 2-bromophenyl | |
| 282 | $C(CH_2)_5$ | 3-bromophenyl | |
| 283 | $C(CH_2)_5$ | 4-bromophenyl | mp. 190-191 |
| 284 | $C(CH_2)_5$ | 2-fluoro-4-bromophenyl | |
| 285 | $C(CH_2)_5$ | 2-trifluoromethylphenyl | |
| 286 | $C(CH_2)_5$ | 3-trifluoromethylphenyl | |
| 287 | $C(CH_2)_5$ | 4-trifluoromethylphenyl | |
| 288 | $C(CH_2)_5$ | 2,4-bis(trifluoromethyl)phenyl | |
| 289 | $C(CH_2)_5$ | 3,5-bis(trifluoromethyl)phenyl | |
| 290 | $C(CH_2)_5$ | 2-methoxyphenyl | |
| 291 | $C(CH_2)_5$ | 3-methoxyphenyl | |
| 292 | $C(CH_2)_5$ | 4-methoxyphenyl | |
| 293 | $C(CH_2)_5$ | 3,4-dimethoxyphenyl | |
| 294 | $C(CH_2)_5$ | 3,4,5-trimethoxyphenyl | |
| 295 | $C(CH_2)_5$ | 4-ethoxyphenyl | |
| 296 | $C(CH_2)_5$ | 4-tetrafluoroethoxyphenyl | |
| 297 | $C(CH_2)_5$ | 4-trifluoromethoxyphenyl | |
| 298 | $C(CH_2)_5$ | 4-methoxyiminocarbyl-phenyl | |
| 299 | $C(CH_2)_5$ | 4-ethoxyiminocarbyl-phenyl | |
| 300 | $C(CH_2)_5$ | 4-methoxy-3-methylphenyl | |
| 301 | $C(CH_2)_5$ | 3-phenoxyphenyl | |
| 302 | $C(CH_2)_5$ | 4-phenoxyphenyl | |
| 303 | $C(CH_2)_5$ | 2-chloro-4-(4'-chlorophenoxy)phenyl | |
| 304 | $C(CH_2)_5$ | 3-(4'-fluorophenoxy)-phenyl | |
| 305 | $C(CH_2)_5$ | 4-benzyloxyphenyl | |
| 306 | $C(CH_3)nC_3H_7$ | phenyl | oil; N-oxide mp. 154-156 |
| 307 | $C(CH_3)nC_3H_7$ | 2-methylphenyl | |
| 308 | $C(CH_3)nC_3H_7$ | 3-methylphenyl | |
| 309 | $C(CH_3)nC_3H_7$ | 4-methylphenyl | |
| 310 | $C(CH_3)nC_3H_7$ | 2,3-dimethylphenyl | |
| 311 | $C(CH_3)nC_3H_7$ | 2,4-dimethylphenyl | |
| 312 | $C(CH_3)nC_3H_7$ | 2,5-dimethylphenyl | |
| 313 | $C(CH_3)nC_3H_7$ | 2,6-dimethylphenyl | |
| 314 | $C(CH_3)nC_3H_7$ | 3,4-dimethylphenyl | |
| 315 | $C(CH_3)nC_3H_7$ | 3,5-dimethylphenyl | |
| 316 | $C(CH_3)nC_3H_7$ | 2,4,5-trimethylphenyl | |
| 317 | $C(CH_3)nC_3H_7$ | 2,4,6-trimethylphenyl | |
| 318 | $C(CH_3)nC_3H_7$ | 2,3,5,6-tetramethylphenyl | |
| 319 | $C(CH_3)nC_3H_7$ | 4-ethylphenyl | |
| 320 | $C(CH_3)nC_3H_7$ | 4-isopropylphenyl | |
| 321 | $C(CH_3)nC_3H_7$ | 4-tert.butylphenyl | |
| 322 | $C(CH_3)nC_3H_7$ | 5-indanyl | |

TABLE 1-continued

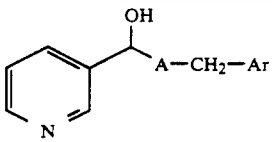

| Ex. no. | A | Ar | Physical data |
|---|---|---|---|
| 323 | C(CH$_3$)nC$_3$H$_7$ | 1-naphthyl | |
| 324 | C(CH$_3$)nC$_3$H$_7$ | 2-naphthyl | |
| 325 | C(CH$_3$)nC$_3$H$_7$ | 2-methyl-1-naphthyl | |
| 326 | C(CH$_3$)nC$_3$H$_7$ | 4-biphenyl | |
| 327 | C(CH$_3$)nC$_3$H$_7$ | 2-fluorophenyl | |
| 328 | C(CH$_3$)nC$_3$H$_7$ | 3-fluorophenyl | |
| 329 | C(CH$_3$)nC$_3$H$_7$ | 4-fluorophenyl | |
| 330 | C(CH$_3$)nC$_3$H$_7$ | 2,3-difluorophenyl | |
| 331 | C(CH$_3$)nC$_3$H$_7$ | 2,4-difluorophenyl | |
| 332 | C(CH$_3$)nC$_3$H$_7$ | 2,5-difluorophenyl | |
| 333 | C(CH$_3$)nC$_3$H$_7$ | 2,6-difluorophenyl | |
| 334 | C(CH$_3$)nC$_3$H$_7$ | 3,4-difluorophenyl | |
| 335 | C(CH$_3$)nC$_3$H$_7$ | 3,5-difluorophenyl | |
| 336 | C(CH$_3$)nC$_3$H$_7$ | 2-fluoro-3-methylphenyl | |
| 337 | C(CH$_3$)nC$_3$H$_7$ | 2,3,5,6-tetrafluorophenyl | |
| 338 | C(CH$_3$)nC$_3$H$_7$ | pentafluorophenyl | |
| 339 | C(CH$_3$)nC$_3$H$_7$ | 2-chlorophenyl | |
| 340 | C(CH$_3$)nC$_3$H$_7$ | 3-chlorophenyl | |
| 341 | C(CH$_3$)nC$_3$H$_7$ | 4-chlorophenyl | oil; N-oxide: mp. 159–160 |
| 342 | C(CH$_3$)nC$_3$H$_7$ | 2,3-dichlorophenyl | |
| 343 | C(CH$_3$)nC$_3$H$_7$ | 2,4-dichlorophenyl | |
| 344 | C(CH$_3$)nC$_3$H$_7$ | 2,5-dichlorophenyl | |
| 345 | C(CH$_3$)nC$_3$H$_7$ | 2,6-dichlorophenyl | |
| 346 | C(CH$_3$)nC$_3$H$_7$ | 3,4-dichlorophenyl | |
| 347 | C(CH$_3$)nC$_3$H$_7$ | 3,5-dichlorophenyl | |
| 348 | C(CH$_3$)nC$_3$H$_7$ | 2,4,5-trichlorophenyl | |
| 349 | C(CH$_3$)nC$_3$H$_7$ | 2,4,6-trichlorophenyl | |
| 350 | C(CH$_3$)nC$_3$H$_7$ | 2,3,6-trichlorophenyl | |
| 351 | C(CH$_3$)nC$_3$H$_7$ | 2-chloro-5-methylphenyl | |
| 352 | C(CH$_3$)nC$_3$H$_7$ | 3-chloro-4-methylphenyl | |
| 353 | C(CH$_3$)nC$_3$H$_7$ | 2-chloro-4-fluorophenyl | |
| 354 | C(CH$_3$)nC$_3$H$_7$ | 2-chloro-6-fluorophenyl | |
| 355 | C(CH$_3$)nC$_3$H$_7$ | 3-chloro-2-fluorophenyl | |
| 356 | C(CH$_3$)nC$_3$H$_7$ | pentachlorophenyl | |
| 357 | C(CH$_3$)nC$_3$H$_7$ | 2-bromophenyl | |
| 358 | C(CH$_3$)nC$_3$H$_7$ | 3-bromophenyl | |
| 359 | C(CH$_3$)nC$_3$H$_7$ | 4-bromophenyl | |
| 360 | C(CH$_3$)nC$_3$H$_7$ | 2-fluoro-4-bromophenyl | |
| 361 | C(CH$_3$)nC$_3$H$_7$ | 2-trifluoromethylphenyl | |
| 362 | C(CH$_3$)nC$_3$H$_7$ | 3-trifluoromethylphenyl | |
| 363 | C(CH$_3$)nC$_3$H$_7$ | 4-trifluoromethylphenyl | |
| 364 | C(CH$_3$)nC$_3$H$_7$ | 2,4-bis(trifluoromethyl)phenyl | |
| 365 | C(CH$_3$)nC$_3$H$_7$ | 3,5-bis(trifluoromethyl)phenyl | |
| 366 | C(CH$_3$)nC$_3$H$_7$ | 2-methoxyphenyl | |
| 367 | C(CH$_3$)nC$_3$H$_7$ | 3-methoxyphenyl | |
| 368 | C(CH$_3$)nC$_3$H$_7$ | 4-methoxyphenyl | |
| 369 | C(CH$_3$)nC$_3$H$_7$ | 3,4-dimethoxyphenyl | |
| 370 | C(CH$_3$)nC$_3$H$_7$ | 3,4,5-trimethoxyphenyl | |
| 371 | C(CH$_3$)nC$_3$H$_7$ | 4-ethoxyphenyl | |
| 372 | C(CH$_3$)nC$_3$H$_7$ | 4-tetrafluoroethoxyphenyl | |
| 373 | C(CH$_3$)nC$_3$H$_7$ | 4-trifluoromethoxyphenyl | |
| 374 | C(CH$_3$)nC$_3$H$_7$ | 4-methoxyiminocarbyl-phenyl | |
| 375 | C(CH$_3$)nC$_3$H$_7$ | 4-ethoxyiminocarbyl-phenyl | |
| 376 | C(CH$_3$)nC$_3$H$_7$ | 4-methoxy-3-methylphenyl | |
| 377 | C(CH$_3$)nC$_3$H$_7$ | 3-phenoxyphenyl | |
| 378 | C(CH$_3$)nC$_3$H$_7$ | 4-phenoxyphenyl | |
| 379 | C(CH$_3$)nC$_3$H$_7$ | 2-chloro-4-(4'-chlorophenoxy)phenyl | |
| 380 | C(CH$_3$)nC$_3$H$_7$ | 3-(4'-fluorophenoxy)-phenyl | |
| 381 | C(CH$_3$)nC$_3$H$_7$ | 4-benzyloxyphenyl | |
| 382 | C(C$_2$H$_5$)nC$_4$H$_9$ | phenyl | oil |
| 383 | C(C$_2$H$_5$)nC$_4$H$_9$ | 2-methylphenyl | |
| 384 | C(C$_2$H$_5$)nC$_4$H$_9$ | 3-methylphenyl | |
| 385 | C(C$_2$H$_5$)nC$_4$H$_9$ | 4-methylphenyl | |
| 386 | C(C$_2$H$_5$)nC$_4$H$_9$ | 2,3-dimethylphenyl | |
| 387 | C(C$_2$H$_5$)nC$_4$H$_9$ | 2,4-dimethylphenyl | |
| 388 | C(C$_2$H$_5$)nC$_4$H$_9$ | 2,5-dimethylphenyl | |
| 389 | C(C$_2$H$_5$)nC$_4$H$_9$ | 2,6-dimethylphenyl | |
| 390 | C(C$_2$H$_5$)nC$_4$H$_9$ | 3,4-dimethylphenyl | |
| 391 | C(C$_2$H$_5$)nC$_4$H$_9$ | 3,5-dimethylphenyl | |
| 392 | C(C$_2$H$_5$)nC$_4$H$_9$ | 2,4,5-trimethylphenyl | |
| 393 | C(C$_2$H$_5$)nC$_4$H$_9$ | 2,4,6-trimethylphenyl | |
| 394 | C(C$_2$H$_5$)nC$_4$H$_9$ | 2,3,5,6-tetramethylphenyl | |
| 395 | C(C$_2$H$_5$)nC$_4$H$_9$ | 4-ethylphenyl | |
| 396 | C(C$_2$H$_5$)nC$_4$H$_9$ | 4-isopropylphenyl | |
| 397 | C(C$_2$H$_5$)nC$_4$H$_9$ | 4-tert.butylphenyl | |
| 398 | C(C$_2$H$_5$)nC$_4$H$_9$ | 5-indanyl | |
| 399 | C(C$_2$H$_5$)nC$_4$H$_9$ | 1-naphthyl | |
| 400 | C(C$_2$H$_5$)nC$_4$H$_9$ | 2-naphthyl | |
| 401 | C(C$_2$H$_5$)nC$_4$H$_9$ | 2-methyl-1-napthyl | |
| 402 | C(C$_2$H$_5$)nC$_4$H$_9$ | 4-biphenyl | |
| 403 | C(C$_2$H$_5$)nC$_4$H$_9$ | 2-fluorophenyl | |
| 404 | C(C$_2$H$_5$)nC$_4$H$_9$ | 3-fluorophenyl | |
| 405 | C(C$_2$H$_5$)nC$_4$H$_9$ | 4-fluorophenyl | |
| 406 | C(C$_2$H$_5$)nC$_4$H$_9$ | 2,3-difluorophenyl | |
| 407 | C(C$_2$H$_5$)nC$_4$H$_9$ | 2,4-difluorophenyl | |
| 408 | C(C$_2$H$_5$)nC$_4$H$_9$ | 2,5-difluorophenyl | |
| 409 | C(C$_2$H$_5$)nC$_4$H$_9$ | 2,6-difluorophenyl | |
| 410 | C(C$_2$H$_5$)nC$_4$H$_9$ | 3,4-difluorophenyl | |
| 411 | C(C$_2$H$_5$)nC$_4$H$_9$ | 3,5-difluorophenyl | |
| 412 | C(C$_2$H$_5$)nC$_4$H$_9$ | 2-fluoro-3-methylphenyl | |
| 413 | C(C$_2$H$_5$)nC$_4$H$_9$ | 2,3,5,6-tetrafluorophenyl | |
| 414 | C(C$_2$H$_5$)nC$_4$H$_9$ | pentafluorophenyl | |
| 415 | C(C$_2$H$_5$)nC$_4$H$_9$ | 2-chlorophenyl | |
| 416 | C(C$_2$H$_5$)nC$_4$H$_9$ | 3-chlorophenyl | |
| 417 | C(C$_2$H$_5$)nC$_4$H$_9$ | 4-chlorophenyl | |
| 418 | C(C$_2$H$_5$)nC$_4$H$_9$ | 2,3-dichlorophenyl | |
| 419 | C(C$_2$H$_5$)nC$_4$H$_9$ | 2,4-dichlorophenyl | |
| 420 | C(C$_2$H$_5$)nC$_4$H$_9$ | 2,5-dichlorophenyl | |
| 421 | C(C$_2$H$_5$)nC$_4$H$_9$ | 2,6-dichlorophenyl | |
| 422 | C(C$_2$H$_5$)nC$_4$H$_9$ | 3,4-dichlorophenyl | |
| 423 | C(C$_2$H$_5$)nC$_4$H$_9$ | 3,5-dichlorophenyl | |
| 424 | C(C$_2$H$_5$)nC$_4$H$_9$ | 2,4,5-trichlorophenyl | |
| 425 | C(C$_2$H$_5$)nC$_4$H$_9$ | 2,4,6-trichlorophenyl | |
| 426 | C(C$_2$H$_5$)nC$_4$H$_9$ | 2,3,6-trichlorophenyl | |
| 427 | C(C$_2$H$_5$)nC$_4$H$_9$ | 2-chloro-5-methylphenyl | |
| 428 | C(C$_2$H$_5$)nC$_4$H$_9$ | 3-chloro-4-methylphenyl | |
| 429 | C(C$_2$H$_5$)nC$_4$H$_9$ | 2-chloro-4-fluorophenyl | |
| 430 | C(C$_2$H$_5$)nC$_4$H$_9$ | 2-chloro-6-fluorophenyl | |
| 431 | C(C$_2$H$_5$)nC$_4$H$_9$ | 3-chloro-2-fluorophenyl | |
| 432 | C(C$_2$H$_5$)nC$_4$H$_9$ | pentachlorophenyl | |
| 433 | C(C$_2$H$_5$)nC$_4$H$_9$ | 2-bromophenyl | |
| 434 | C(C$_2$H$_5$)nC$_4$H$_9$ | 3-bromophenyl | |
| 435 | C(C$_2$H$_5$)nC$_4$H$_9$ | 4-bromophenyl | |
| 436 | C(C$_2$H$_5$)nC$_4$H$_9$ | 2-fluoro-4-bromophenyl | |
| 437 | C(C$_2$H$_5$)nC$_4$H$_9$ | 2-trifluoromethylphenyl | |
| 438 | C(C$_2$H$_5$)nC$_4$H$_9$ | 3-trifluoromethylphenyl | |
| 439 | C(C$_2$H$_5$)nC$_4$H$_9$ | 4-trifluoromethylphenyl | |
| 440 | C(C$_2$H$_5$)nC$_4$H$_9$ | 2,4-bis(trifluoromethyl)phenyl | |
| 441 | C(C$_2$H$_5$)nC$_4$H$_9$ | 3,5-bis(trifluoromethyl)phenyl | |
| 442 | C(C$_2$H$_5$)nC$_4$H$_9$ | 2-methoxyphenyl | |
| 443 | C(C$_2$H$_5$)nC$_4$H$_9$ | 3-methoxyphenyl | |
| 444 | C(C$_2$H$_5$)nC$_4$H$_9$ | 4-methoxyphenyl | |
| 445 | C(C$_2$H$_5$)nC$_4$H$_9$ | 3,4-dimethoxyphenyl | |
| 446 | C(C$_2$H$_5$)nC$_4$H$_9$ | 3,4,5-trimethoxyphenyl | |
| 447 | C(C$_2$H$_5$)nC$_4$H$_9$ | 4-ethoxyphenyl | |
| 448 | C(C$_2$H$_5$)nC$_4$H$_9$ | 4-tetrafluoroethoxyphenyl | |
| 449 | C(C$_2$H$_5$)nC$_4$H$_9$ | 4-trifluoromethoxyphenyl | |
| 450 | C(C$_2$H$_5$)nC$_4$H$_9$ | 4-methoxyiminocarbyl-phenyl | |
| 451 | C(C$_2$H$_5$)nC$_4$H$_9$ | 4-ethoxyiminocarbyl-phenyl | |
| 452 | C(C$_2$H$_5$)nC$_4$H$_9$ | 4-methoxy-3-methylphenyl | |
| 453 | C(C$_2$H$_5$)nC$_4$H$_9$ | 3-phenoxyphenyl | |
| 454 | C(C$_2$H$_5$)nC$_4$H$_9$ | 4-phenoxyphenyl | |
| 455 | C(C$_2$H$_5$)nC$_4$H$_9$ | 2-chloro-4-(4'-chlorophenoxy)phenyl | |
| 456 | C(C$_2$H$_5$)nC$_4$H$_9$ | 3-(4'-fluorophenoxy)-phenyl | |
| 457 | C(C$_2$H$_5$)nC$_4$H$_9$ | 4-benzyloxyphenyl | |
| 458 | C(CH$_2$)$_3$OCH$_2$ | phenyl | |
| 459 | C(CH$_2$)$_3$OCH$_2$ | 2-methylphenyl | |

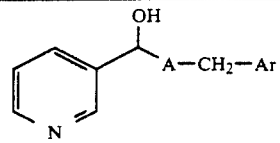

TABLE 1-continued

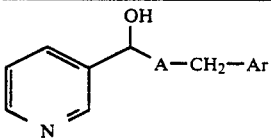

| Ex. no. | A | Ar | Physical data |
|---|---|---|---|
| 460 | C(CH$_2$)$_3$OCH$_2$ | 3-methylphenyl | |
| 461 | C(CH$_2$)$_3$OCH$_2$ | 4-methylphenyl | |
| 462 | C(CH$_2$)$_3$OCH$_2$ | 2,3-dimethylphenyl | |
| 463 | C(CH$_2$)$_3$OCH$_2$ | 2,4-dimethylphenyl | |
| 464 | C(CH$_2$)$_3$OCH$_2$ | 2,5-dimethylphenyl | |
| 465 | C(CH$_2$)$_3$OCH$_2$ | 2,6-dimethylphenyl | |
| 466 | C(CH$_2$)$_3$OCH$_2$ | 3,4-dimethylphenyl | |
| 467 | C(CH$_2$)$_3$OCH$_2$ | 3,5-dimethylphenyl | |
| 468 | C(CH$_2$)$_3$OCH$_2$ | 2,4,5-trimethylphenyl | |
| 469 | C(CH$_2$)$_3$OCH$_2$ | 2,4,6-trimethylphenyl | |
| 470 | C(CH$_2$)$_3$OCH$_2$ | 2,3,5,6-tetramethylphenyl | |
| 471 | C(CH$_2$)$_3$OCH$_2$ | 4-ethylphenyl | |
| 472 | C(CH$_2$)$_3$OCH$_2$ | 4-isopropylphenyl | |
| 473 | C(CH$_2$)$_3$OCH$_2$ | 4-tert.butylphenyl | |
| 474 | C(CH$_2$)$_3$OCH$_2$ | 5-indanyl | |
| 475 | C(CH$_2$)$_3$OCH$_2$ | 1-naphthyl | |
| 476 | C(CH$_2$)$_3$OCH$_2$ | 2-naphthyl | |
| 477 | C(CH$_2$)$_3$OCH$_2$ | 2-methyl-1-naphthyl | |
| 478 | C(CH$_2$)$_3$OCH$_2$ | 4-biphenyl | |
| 479 | C(CH$_2$)$_3$OCH$_2$ | 2-fluorophenyl | |
| 480 | C(CH$_2$)$_3$OCH$_2$ | 3-fluorophenyl | |
| 481 | C(CH$_2$)$_3$OCH$_2$ | 4-fluorophenyl | |
| 482 | C(CH$_2$)$_3$OCH$_2$ | 2,3-difluorophenyl | |
| 483 | C(CH$_2$)$_3$OCH$_2$ | 2,4-difluorophenyl | |
| 484 | C(CH$_2$)$_3$OCH$_2$ | 2,5-difluorophenyl | |
| 485 | C(CH$_2$)$_3$OCH$_2$ | 2,6-difluorophenyl | |
| 486 | C(CH$_2$)$_3$OCH$_2$ | 3,4-difluorophenyl | |
| 487 | C(CH$_2$)$_3$OCH$_2$ | 3,5-difluorophenyl | |
| 488 | C(CH$_2$)$_3$OCH$_2$ | 2-fluoro-3-methylphenyl | |
| 489 | C(CH$_2$)$_3$OCH$_2$ | 2,3,5,6-tetrafluorophenyl | |
| 490 | C(CH$_2$)$_3$OCH$_2$ | pentafluorophenyl | |
| 491 | C(CH$_2$)$_3$OCH$_2$ | 2-chlorophenyl | |
| 492 | C(CH$_2$)$_3$OCH$_2$ | 3-chlorophenyl | |
| 493 | C(CH$_2$)$_3$OCH$_2$ | 4-chlorophenyl | |
| 494 | C(CH$_2$)$_3$OCH$_2$ | 2,3-dichlorophenyl | |
| 495 | C(CH$_2$)$_3$OCH$_2$ | 2,4-dichlorophenyl | |
| 496 | C(CH$_2$)$_3$OCH$_2$ | 2,5-dichlorophenyl | |
| 497 | C(CH$_2$)$_3$OCH$_2$ | 2,6-dichlorophenyl | |
| 498 | C(CH$_2$)$_3$OCH$_2$ | 3,4-dichlorophenyl | |
| 499 | C(CH$_2$)$_3$OCH$_2$ | 3,5-dichlorophenyl | |
| 500 | C(CH$_2$)$_3$OCH$_2$ | 2,4,5-trichlorophenyl | |
| 501 | C(CH$_2$)$_3$OCH$_2$ | 2,4,6-trichlorophenyl | |
| 502 | C(CH$_2$)$_3$OCH$_2$ | 2,3,6-trichlorophenyl | |
| 503 | C(CH$_2$)$_3$OCH$_2$ | 2-chloro-5-methylphenyl | |
| 504 | C(CH$_2$)$_3$OCH$_2$ | 3-chloro-4-methylphenyl | |
| 505 | C(CH$_2$)$_3$OCH$_2$ | 2-chloro-4-fluorophenyl | |
| 506 | C(CH$_2$)$_3$OCH$_2$ | 2-chloro-6-fluorophenyl | |
| 507 | C(CH$_2$)$_3$OCH$_2$ | 3-chloro-2-fluorophenyl | |
| 508 | C(CH$_2$)$_3$OCH$_2$ | pentachlorophenyl | |
| 509 | C(CH$_2$)$_3$OCH$_2$ | 2-bromophenyl | |
| 510 | C(CH$_2$)$_3$OCH$_2$ | 3-bromophenyl | |
| 511 | C(CH$_2$)$_3$OCH$_2$ | 4-bromophenyl | |
| 512 | C(CH$_2$)$_3$OCH$_2$ | 2-fluoro-4-bromophenyl | |
| 513 | C(CH$_2$)$_3$OCH$_2$ | 2-trifluoromethylphenyl | |
| 514 | C(CH$_2$)$_3$OCH$_2$ | 3-trifluoromethylphenyl | |
| 515 | C(CH$_2$)$_3$OCH$_2$ | 4-trifluoromethylphenyl | |
| 516 | C(CH$_2$)$_3$OCH$_2$ | 2,4-bis(trifluoromethyl)phenyl | |
| 517 | C(CH$_2$)$_3$OCH$_2$ | 3,5-bis(trifluoromethyl)phenyl | |
| 518 | C(CH$_2$)$_3$OCH$_2$ | 2-methoxyphenyl | |
| 519 | C(CH$_2$)$_3$OCH$_2$ | 3-methoxyphenyl | |
| 520 | C(CH$_2$)$_3$OCH$_2$ | 4-methoxyphenyl | |
| 521 | C(CH$_2$)$_3$OCH$_2$ | 3,4-dimethoxyphenyl | |
| 522 | C(CH$_2$)$_3$OCH$_2$ | 3,4,5-trimethoxyphenyl | |
| 523 | C(CH$_2$)$_3$OCH$_2$ | 4-ethoxyphenyl | |
| 524 | C(CH$_2$)$_3$OCH$_2$ | 4-tetrafluoroethoxyphenyl | |
| 525 | C(CH$_2$)$_3$OCH$_2$ | 4-trifluoromethoxyphenyl | |
| 526 | C(CH$_2$)$_3$OCH$_2$ | 4-methoxyiminocarbyl-phenyl | |
| 527 | C(CH$_2$)$_3$OCH$_2$ | 4-ethoxyiminocarbyl-phenyl | |
| 528 | C(CH$_2$)$_3$OCH$_2$ | 4-methoxy-3-methylphenyl | |
| 529 | C(CH$_2$)$_3$OCH$_2$ | 3-phenoxyphenyl | |
| 530 | C(CH$_2$)$_3$OCH$_2$ | 4-phenoxyphenyl | |
| 531 | C(CH$_2$)$_3$OCH$_2$ | 2-chloro-4-(4'-chlorophenoxy)phenyl | |
| 532 | C(CH$_2$)$_3$OCH$_2$ | 3-(4'-fluorophenoxy)-phenyl | |
| 533 | C(CH$_2$)$_3$OCH$_2$ | 4-benzyloxyphenyl | |
| 534 | C(CH$_2$)$_2$ | phenyl | |
| 535 | C(CH$_2$)$_2$ | 2-methylphenyl | |
| 536 | C(CH$_2$)$_2$ | 3-methylphenyl | |
| 537 | C(CH$_2$)$_2$ | 4-methylphenyl | |
| 538 | C(CH$_2$)$_2$ | 2,3-dimethylphenyl | |
| 539 | C(CH$_2$)$_2$ | 2,4-dimethylphenyl | |
| 540 | C(CH$_2$)$_2$ | 2,5-dimethylphenyl | |
| 541 | C(CH$_2$)$_2$ | 2,6-dimethylphenyl | |
| 542 | C(CH$_2$)$_2$ | 3,4-dimethylphenyl | |
| 543 | C(CH$_2$)$_2$ | 3,5-dimethylphenyl | |
| 544 | C(CH$_2$)$_2$ | 2,4,5-trimethylphenyl | |
| 545 | C(CH$_2$)$_2$ | 2,4,6-trimethylphenyl | |
| 546 | C(CH$_2$)$_2$ | 2,3,5-tetramethylphenyl | |
| 547 | C(CH$_2$)$_2$ | 4-ethylphenyl | |
| 548 | C(CH$_2$)$_2$ | 4-isopropylphenyl | |
| 549 | C(CH$_2$)$_2$ | 4-tert.butylphenyl | |
| 550 | C(CH$_2$)$_2$ | 5-indanyl | |
| 551 | C(CH$_2$)$_2$ | 1-naphthyl | |
| 552 | C(CH$_2$)$_2$ | 2-naphthyl | |
| 553 | C(CH$_2$)$_2$ | 2-methyl-1-napthyl | |
| 554 | C(CH$_2$)$_2$ | 4-biphenyl | |
| 555 | C(CH$_2$)$_2$ | 2-fluorophenyl | |
| 556 | C(CH$_2$)$_2$ | 3-fluorophenyl | |
| 557 | C(CH$_2$)$_2$ | 4-fluorophenyl | |
| 558 | C(CH$_2$)$_2$ | 2,3-difluorophenyl | |
| 559 | C(CH$_2$)$_2$ | 2,4-difluorophenyl | |
| 560 | C(CH$_2$)$_2$ | 2,5-difluorophenyl | |
| 561 | C(CH$_2$)$_2$ | 2,6-difluorophenyl | |
| 562 | C(CH$_2$)$_2$ | 3,4-difluorophenyl | |
| 563 | C(CH$_2$)$_2$ | 3,5-difluorophenyl | |
| 564 | C(CH$_2$)$_2$ | 2-fluoro-3-methylphenyl | |
| 565 | C(CH$_2$)$_2$ | 2,3,5,6-tetrafluorophenyl | |
| 566 | C(CH$_2$)$_2$ | pentafluorophenyl | |
| 567 | C(CH$_2$)$_2$ | 2-chlorophenyl | |
| 568 | C(CH$_2$)$_2$ | 3-chlorophenyl | |
| 569 | C(CH$_2$)$_2$ | 4-chlorophenyl | |
| 570 | C(CH$_2$)$_2$ | 2,3-dichlorophenyl | |
| 571 | C(CH$_2$)$_2$ | 2,4-dichlorophenyl | |
| 572 | C(CH$_2$)$_2$ | 2,5-dichlorophenyl | |
| 573 | C(CH$_2$)$_2$ | 2,6-dichlorophenyl | |
| 574 | C(CH$_2$)$_2$ | 3,4-dichlorophenyl | |
| 575 | C(CH$_2$)$_2$ | 3,5-dichlorophenyl | |
| 576 | C(CH$_2$)$_2$ | 2,4,5-trichlorophenyl | |
| 577 | C(CH$_2$)$_2$ | 2,4,6-trichlorophenyl | |
| 578 | C(CH$_2$)$_2$ | 2,3,6-trichlorophenyl | |
| 579 | C(CH$_2$)$_2$ | 2-chloro-5-methylphenyl | |
| 580 | C(CH$_2$)$_2$ | 3-chloro-4-methylphenyl | |
| 581 | C(CH$_2$)$_2$ | 2-chloro-4-fluorophenyl | |
| 582 | C(CH$_2$)$_2$ | 2-chloro-6-fluorophenyl | |
| 583 | C(CH$_2$)$_2$ | 3-chloro-2-fluorophenyl | |
| 584 | C(CH$_2$)$_2$ | pentachlorophenyl | |
| 585 | C(CH$_2$)$_2$ | 2-bromophenyl | |
| 586 | C(CH$_2$)$_2$ | 3-bromophenyl | |
| 587 | C(CH$_2$)$_2$ | 4-bromophenyl | |
| 588 | C(CH$_2$)$_2$ | 2-fluoro-4-bromophenyl | |
| 589 | C(CH$_2$)$_2$ | 2-trifluoromethylphenyl | |
| 590 | C(CH$_2$)$_2$ | 3-trifluoromethylphenyl | |
| 591 | C(CH$_2$)$_2$ | 4-trifluoromethylphenyl | |
| 592 | C(CH$_2$)$_2$ | 2,4-bis(trifluoromethyl)phenyl | |
| 593 | C(CH$_2$)$_2$ | 3,5-bis(trifluoromethyl)phenyl | |
| 594 | C(CH$_2$)$_2$ | 2-methoxyphenyl | |
| 595 | C(CH$_2$)$_2$ | 3-methoxyphenyl | |
| 596 | C(CH$_2$)$_2$ | 4-methoxyphenyl | |
| 597 | C(CH$_2$)$_2$ | 3,4-dimethoxyphenyl | |
| 598 | C(CH$_2$)$_2$ | 3,4,5-trimethoxyphenyl | |
| 599 | C(CH$_2$)$_2$ | 4-ethoxyphenyl | |
| 600 | C(CH$_2$)$_2$ | 4-tetrafluoroethoxyphenyl | |
| 601 | C(CH$_2$)$_2$ | 4-trifluoromethoxyphenyl | |

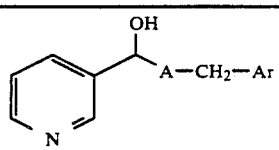

TABLE 1-continued

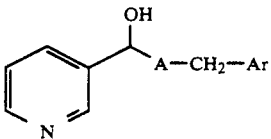

| Ex. no. | A | Ar | Physical data |
|---|---|---|---|
| 602 | C(CH$_2$)$_2$ | 4-methoxyiminocarbyl-phenyl | |
| 603 | C(CH$_2$)$_2$ | 4-ethoxyiminocarbyl-phenyl | |
| 604 | C(CH$_2$)$_2$ | 4-methoxy-3-methylphenyl | |
| 605 | C(CH$_2$)$_2$ | 3-phenoxyphenyl | |
| 606 | C(CH$_2$)$_2$ | 4-phenoxyphenyl | |
| 607 | C(CH$_2$)$_2$ | 2-chloro-4-(4'-chloro-phenoxy)phenyl | |
| 608 | C(CH$_2$)$_2$ | 3-(4'-fluorophenoxy)-phenyl | |
| 609 | C(CH$_2$)$_2$ | 4-benzyloxyphenyl | |

TABLE 2

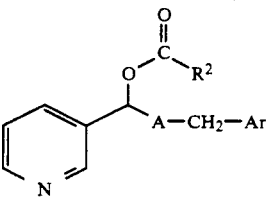

| Ex. no. | R$^2$ | A | Ar | Physical data |
|---|---|---|---|---|
| 610 | CH$_3$ | C(C$_2$H$_5$)$_2$ | phenyl | oil |
| 611 | CH$_3$ | C(C$_2$H$_5$)$_2$ | 4-chlorophenyl | oil |
| 612 | CH$_3$ | C(C$_2$H$_5$)$_2$ | 4-fluorophenyl | oil |
| 613 | CH$_3$ | C(C$_2$H$_5$)$_2$ | 2,4-dichlorophenyl | oil |
| 614 | CH$_3$ | C(C$_2$H$_5$)$_2$ | 2-methylphenyl | |
| 615 | CH$_3$ | C(C$_2$H$_5$)$_2$ | 4-methylphenyl | |
| 616 | CH$_3$ | C(C$_2$H$_5$)$_2$ | 4-tert.-butylphenyl | |
| 617 | CH$_3$ | C(C$_2$H$_5$)$_2$ | 2-naphthyl | |
| 618 | CH$_3$ | C(C$_2$H$_5$)$_2$ | 2-fluorophenyl | |
| 619 | CH$_3$ | C(C$_2$H$_5$)$_2$ | 4-bromophenyl | |
| 620 | CH$_3$ | C(C$_2$H$_5$)$_2$ | 3-fluorophenyl | |
| 621 | CH$_3$ | C(C$_2$H$_5$)$_2$ | 3,4-dichlorophenyl | |
| 622 | CH$_3$ | C(CH$_2$)$_5$ | phenyl | |
| 623 | CH$_3$ | C(CH$_2$)$_5$ | 2-methylphenyl | |
| 624 | CH$_3$ | C(CH$_2$)$_5$ | 4-methylphenyl | |
| 625 | CH$_3$ | C(CH$_2$)$_5$ | 4-tert.-butylphenyl | |
| 626 | CH$_3$ | C(CH$_2$)$_5$ | 2-naphthyl | |
| 627 | CH$_3$ | C(CH$_2$)$_5$ | 2-fluorophenyl | |
| 628 | CH$_3$ | C(CH$_2$)$_5$ | 3-fluorophenyl | |
| 629 | CH$_3$ | C(CH$_2$)$_5$ | 4-fluorophenyl | |
| 630 | CH$_3$ | C(CH$_2$)$_5$ | 4-bromophenyl | |
| 631 | CH$_3$ | C(CH$_2$)$_5$ | 4-chlorophenyl | |
| 632 | CH$_3$ | C(CH$_2$)$_5$ | 2-chlorophenyl | |
| 633 | CH$_3$ | C(CH$_2$)$_5$ | 2,4-dichlorophenyl | |
| 634 | CH$_3$ | C(CH$_2$)$_5$ | 3,4-dichlorophenyl | |
| 635 | CH$_3$ | C(CH$_2$)$_4$ | phenyl | |
| 636 | CH$_3$ | C(CH$_2$)$_4$ | 2-methylphenyl | |
| 637 | CH$_3$ | C(CH$_2$)$_4$ | 4-methylphenyl | |
| 638 | CH$_3$ | C(CH$_2$)$_4$ | 4-tert.-butylphenyl | |
| 639 | CH$_3$ | C(CH$_2$)$_4$ | 2-naphthyl | |
| 640 | CH$_3$ | C(CH$_2$)$_4$ | 2-fluorophenyl | |
| 641 | CH$_3$ | C(CH$_2$)$_4$ | 3-fluorophenyl | |
| 642 | CH$_3$ | C(CH$_2$)$_4$ | 4-fluorophenyl | |
| 643 | CH$_3$ | C(CH$_2$)$_4$ | 4-bromophenyl | |
| 644 | CH$_3$ | C(CH$_2$)$_4$ | 4-chlorophenyl | |
| 645 | CH$_3$ | C(CH$_2$)$_4$ | 2-chlorophenyl | |
| 646 | CH$_3$ | C(CH$_2$)$_4$ | 2,4-dichlorophenyl | |
| 647 | CH$_3$ | C(CH$_2$)$_4$ | 3,4-dichlorophenyl | |
| 648 | CH$_3$ | C(C$_2$H$_5$)$^n$C$_4$H$_9$ | phenyl | |
| 649 | CH$_3$ | C(C$_2$H$_5$)$^n$C$_4$H$_9$ | 2-methylphenyl | |
| 650 | CH$_3$ | C(C$_2$H$_5$)$^n$C$_4$H$_9$ | 4-methylphenyl | |
| 651 | CH$_3$ | C(C$_2$H$_5$)$^n$C$_4$H$_9$ | 4-tert.-butylphenyl | |
| 652 | CH$_3$ | C(C$_2$H$_5$)$^n$C$_4$H$_9$ | 2-naphthyl | |
| 653 | CH$_3$ | C(C$_2$H$_5$)$^n$C$_4$H$_9$ | 2-fluorophenyl | |
| 654 | CH$_3$ | C(C$_2$H$_5$)$^n$C$_4$H$_9$ | 3-fluorophenyl | |
| 655 | CH$_3$ | C(C$_2$H$_5$)$^n$C$_4$H$_9$ | 4-fluorophenyl | |

TABLE 2-continued

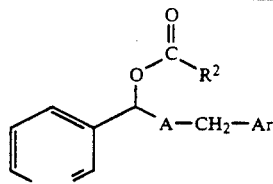

| Ex. no. | R$^2$ | A | Ar | Physical data |
|---|---|---|---|---|
| 656 | CH$_3$ | C(C$_2$H$_5$)$^n$C$_4$H$_9$ | 4-bromophenyl | |
| 657 | CH$_3$ | C(C$_2$H$_5$)$^n$C$_4$H$_9$ | 4-chlorophenyl | |
| 658 | CH$_3$ | C(C$_2$H$_5$)$^n$C$_4$H$_9$ | 2,4-dichlorophenyl | |
| 659 | CH$_3$ | C(C$_2$H$_5$)$^n$C$_4$H$_9$ | 3,4-dichlorophenyl | |
| 660 | CH$_3$ | C(C$_2$H$_5$)$^n$C$_4$H$_9$ | 4-biphenyl | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in vegetables and fruit.

The compounds are applied by spraying or dusting the plants with the active ingredients, or treating the seeds of the plants with the active ingredients. They may be applied before or after infection of the plants or seeds by the fungi. Either the fungi, or the plants, seed, materials or soil to be protected against fungus attack are treated with a fungicidally effective amount of the active ingredient.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials (wood), for example against *Paecilomyces variotii*.

When the active ingredients are used for treating seed, amounts of from 0.001 to 50, and preferably from 0.01 to 10, g are generally used per kg of seed.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 230 (Table 1) is mixed with 10 parts by weight of N-methyl-α-pyrrolidone. A mixture is obtained which is suitable for application in the form of very fine drops.

II. 20 parts by weight of compound no. 306 (Table 1) is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 341 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 382 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 175 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 187 is intimately mixed with 97 parts by weight of particulate kaolin. A dust is obtained containing 3% by weight of the active ingredient.

VII. 30 parts by weight of compound no. 191 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 253 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 267 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

USE EXAMPLES

For comparison purposes, the compound 3-phenyl-2,2-dimethyl-1-(3-pyridyl)propan-1-ol (A) disclosed in EP 302,365 was used.

USE EXAMPLE 1

Action on *Botrytis cinerea* in pimientos

Pimiento seedlings of the "Neusiedler Ideal Elite" variety with 4 to 5 well developed leaves were sprayed to runoff with aqueous suspensions containing (dry basis) 80% of active ingredient and 20% of emulsifier. After the sprayed-on layer had dried, the plants were sprayed with a conidial suspension of the fungus *Botrytis cinerea* and kept in a high-humidity chamber at 22° to 24° C. After 5 days, the disease had spread on the untreated control plants to such an extent that the necroses covered the major portion of the leaves. The leaf attack was assessed.

The results show that active ingredients 230, 306, 341 and 382, applied as 0.05% spray liquors, have a better fungicidal action (90%) than prior art active ingredient A (55%).

USE EXAMPLE 2

Action on *Pyrenophora teres*

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus *Pyrenophora teres*, and set up for 48 hours in a high-humidity climatic cabinet at 18° C. The plants were then cultivated for a further 5 days in the greenhouse at 20° to 22° C. and a relative humidity of 70° C. The extent of fungus spread was then assessed.

The results show that active ingredients 175, 187, 191, 253, 267, 306, 341 and 382, applied as 0.025% spray liquors, have a better fungicidal action (98%) than prior art active ingredient A (60%).

We claim:

1. A pyridine compound having the following formula:

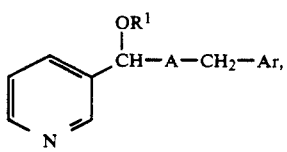

where $R^1$ is hydrogen or an acyl radical $—COR^2$; $R^2$ is $C_1-C_6$-alkyl, $C_3-C_6$-alkenyl, $C_3-C_6$-alkynyl, $C_1-C_6$-haloalkyl or substituted or unsubstituted aryl; A is one of the groups

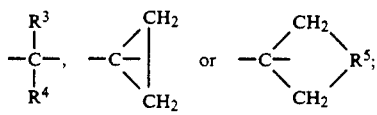

where $R^3$ and $R^4$ are identical or differ and each is $C_1-C_6$-alkyl, with the proviso that $R^3$ and $R^4$ are not simultaneously methyl; $R^5$ is one of the groups $(CH_2)_n$, $CH_2OCH_2$, $CH_2S(O)_mCH_2$, $CH_2CH_2O$ or $CH_2CH_2S(O)_m$, n denoting 1, 2, 3, 4 or 5, and m being 0, 1 or 2; Ar is phenyl, indanyl, 1-naphthyl, 2-naphthyl, 2-methyl-1-naphthyl or phenyl substituted by one to five substituents selected from the group consisting of $C_1-C_6$-alkyl, phenyl, halogen, $C_1-C_6$-haloalkyl, $C_1-C_6$-alkoxy, $C_1-C_6$-haloalkoxy, $C_1-C_6$-alkoxyiminocarbyl, phenoxy, halophenoxy and benzyloxy, or the N-oxide or plant-tolerated acid addition salt thereof.

2. A fungicidal composition containing a carrier and a fungicidally effective amount of a pyridine compound of the formula

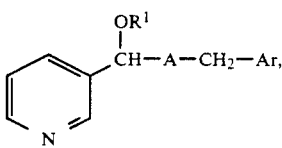

where $R^1$ is hydrogen or an acyl radical $—COR^2$; $R^2$ is $C_1-C_6$-alkyl, $C_3-C_6$-alkenyl, $C_3-C_6$-alkynyl, $C_1-C_6$-haloalkyl or substituted or unsubstituted aryl; A is one of the groups

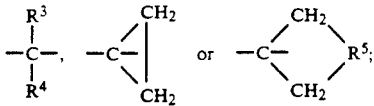

where $R^3$ and $R^4$ are identical or differ and each is $C_1-C_6$-alkyl, with the proviso that $R^3$ and $R^4$ are not simultaneously methyl; $R^5$ is one of the groups $(CH_2)_n$, $CH_2OCH_2$, $CH_2S(O)_mCH_2$, $CH_2CH_2O$ or $CH_2CH_2S(O)_m$, n denoting 1, 2, 3, 4 or 5, and m being 0, 1 or 2; Ar is phenyl, indanyl, 1-naphthyl, 2-naphthyl, 2-methyl-1-naphthyl or phenyl substituted by one to five substituents selected from the group consisting of $C_1-C_6$-alkyl, phenyl, halogen, $C_1-C_6$-haloalkyl, $C_1-C_6$-alkoxy, $C_1-C_6$-haloalkoxy, $C_1-C_6$-alkoxyiminocarbyl, phenoxy, halophenoxy and benzyloxy, or the N-oxide or plant-tolerated acid addition salt thereof.

3. A process for combating fungi, wherein the fungi, or the materials, plants, soils or seed threatened by fungus attack are treated with a fungicidally effective amount of a pyridine compound of the formula

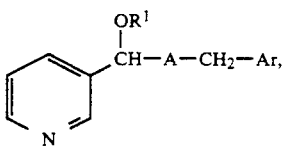

where $R^1$ is hydrogen or an acyl radical $—COR^2$; $R^2$ is $C_1-C_6$-alkyl, $C_3-C_6$-alkenyl, $C_3-C_6$-alkynyl, $C_1-C_6$-haloalkyl or substituted or unsubstituted aryl; A is one of the groups

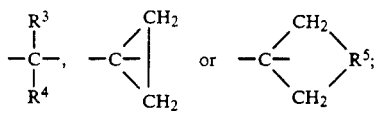

where $R^3$ and $R^4$ are identical or differ and each is $C_1-C_6$-alkyl, with the proviso that $R^3$ and $R^4$ are not simultaneously methyl; $R^5$ is one of the groups $(CH_2)_n$, $CH_2OCH_2$, $CH_2S(O)_mCH_2$, $CH_2CH_2O$ or $CH_2CH_2S(O)_m$, n denoting 1, 2, 3, 4 or 5, and m being 0, 1 or 2; Ar is phenyl, indanyl, 1-naphthyl, 2-naphthyl, 2-methyl-1-naphthyl or phenyl substituted by one to five substituents selected from the group consisting of $C_1-C_6$-alkyl, phenyl, halogen, $C_1-C_6$-haloalkyl, $C_1-C_6$-alkoxy, $C_1-C_6$-haloalkoxy, $C_1-C_6$-alkoxyiminocarbyl, phenoxy, halophenoxy and benzyloxy, or the N-oxide or plant-tolerated acid addition salt thereof.

* * * * *